United States Patent [19]

Ciaglia

[11] Patent Number: 5,217,007
[45] Date of Patent: Jun. 8, 1993

[54] SPECULUM FOR FORMING AN OSTOMY IN A TRACHEA

[75] Inventor: Pasquale Ciaglia, Utica, N.Y.

[73] Assignee: Cook Incorporated, Bloomington, Ind.

[21] Appl. No.: 692,222

[22] Filed: Apr. 26, 1991

[51] Int. Cl.$^5$ .................... A61M 16/00; A61M 29/00
[52] U.S. Cl. .................... 128/207.29; 128/200.26; 606/198; 606/207
[58] Field of Search .................. 128/200.24, 200.26, 128/207.29, 3, 17, 18, 19; 606/185, 198, 207; 604/158, 164, 264, 272, 273, 104, 106

[56] References Cited

U.S. PATENT DOCUMENTS

| | | | |
|---|---|---|---|
| D. 300,244 | 3/1989 | Onejola | 606/185 |
| 605,652 | 6/1898 | Pitt | 128/18 |
| 1,097,978 | 5/1914 | Johnson | 606/198 |
| 1,328,624 | 1/1920 | Graham | 606/198 |
| 2,483,233 | 9/1949 | Price et al. | 128/17 |
| 2,601,513 | 6/1952 | Gladstone | 606/207 |
| 2,672,859 | 3/1954 | Jones | 128/17 |
| 2,743,726 | 5/1956 | Grieshaber | 606/207 |
| 3,550,584 | 12/1970 | Ring | 128/17 |
| 4,300,564 | 11/1981 | Furihata | 606/207 |
| 4,449,532 | 5/1984 | Storz | 606/191 |
| 4,520,810 | 6/1985 | Weiss | 128/200.26 |
| 4,643,188 | 2/1987 | Weiss | 128/305 |
| 4,677,978 | 7/1987 | Melker | 128/207.14 |
| 4,693,250 | 9/1987 | Coons | 606/198 |
| 4,889,112 | 12/1989 | Schachner et al. | 128/200.26 |
| 4,971,036 | 11/1990 | Collins | 128/3 |

FOREIGN PATENT DOCUMENTS

| | | | |
|---|---|---|---|
| 157458 | 10/1962 | U.S.S.R. | 128/200.26 |
| 275298 | 10/1970 | U.S.S.R. | 128/17 |

OTHER PUBLICATIONS

Jacobs et al., "Transtracheal Catheter Ventilation . . . ", *Chest*, vol. 65, No. 1, Jan. 1974, pp. 36-40.
*Eye, Ear, Nose & Throat Catalogue*, pp. 232 & 233, V. Mueller & Co., Chicago, IL, USA, Dec. 1939.
Schachner, A. et al., "Rapid Percutaneous Tracheostomy," *Chest*, 98:5, Nov. 1990, pp. 1266-1270.
Griggs, W. M. et al., "A Simple Percutaneous Tracheostomy Technique," *Surgery, Gynecology & Obstetrics*, vol. 170, Jun. 1990, pp. 543-545.
Ovil, Y., "Surgical Pros and Cons," *Surgery, Gynecology & Obstetrics*, Apr. 1991, vol. 172, pp. 307-308.

(List continued on next page.)

Primary Examiner—David A. Wiecking
Assistant Examiner—Kimberly L. Asher
Attorney, Agent, or Firm—Richard J. Godlewski

[57] ABSTRACT

A speculum for forming an ostomy in a trachea. The speculum includes a pair of opposing, pivotally interconnected elongated members and respective distal nose portions extending distally from the elongated members. The elongated members have respective proximal handle portions of which the distal nose portions extend laterally therefrom. One of the nose portions includes a tubular member with a flexible distal end that has a preformed curve and extends distally beyond the other nose portion. A cannula is inserted entirely through the passageway of the tubular member to extend distally therefrom and straighten the preformed curve of the tubular member for insertion into the trachea. The cannula and tubular member are inserted into the trachea to form an opening to the air passageway of the trachea. Proper placement is detected with formation of air bubbles in the chamber of a syringe connected to the proximal end of the cannula. The cannula is removed from the tubular member allowing the tubular member to assume the preformed curve for preventing injury to the posterior wall of the trachea. The distal nose portions of the speculum are then inserted through the opening into the air passageway of the trachea. The distal nose portions are spread apart in both a longitudinal and a lateral direction to dilate the opening and permit insertion of an ostomy tube into the trachea. With the ostomy tube positioned in the trachea, the speculum is removed from the opening.

20 Claims, 6 Drawing Sheets

OTHER PUBLICATIONS

Griggs, W. M. et al., "Surgical Pros and Cons," *Surgery, Gynecology & Obstetrics*, Apr. 1991, vol. 172, pp. 307-308.

Ciaglia, P. et al., "Emergency Percutaneous Dilatational Cricothyroidostomy; Use of Modified Nasal Speculum," Presented at 3rd International Conference on Emergency Medicine, Toronto, Canada, Jun. 25, 1990.

Ciaglia, P. et al., "Emergency Percutaneous Dilatational Cricothyroidostomy," *Critical Care Medicine*, Apr. 1990, p. S224.

Ciaglia, P. et al., "Surgical Pros and Cons," *Surgery, Gynecology & Obstetrics*, Dec. 1990, vol. 171, pp. 511-512.

Ciaglia, P. et al., "Elective Percutaneous Dilatational Tracheostomy: A New Simple Bedside Procedure; Preliminary Report," *Chest*, Jun. 1985, vol. 87, pp. 715-719.

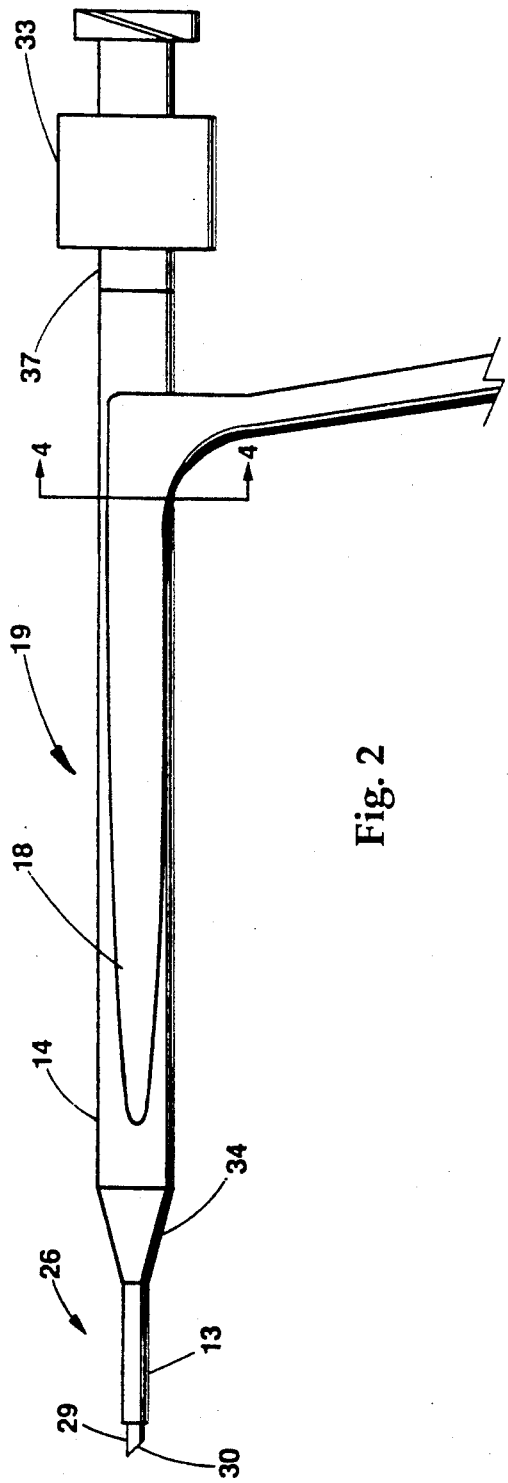
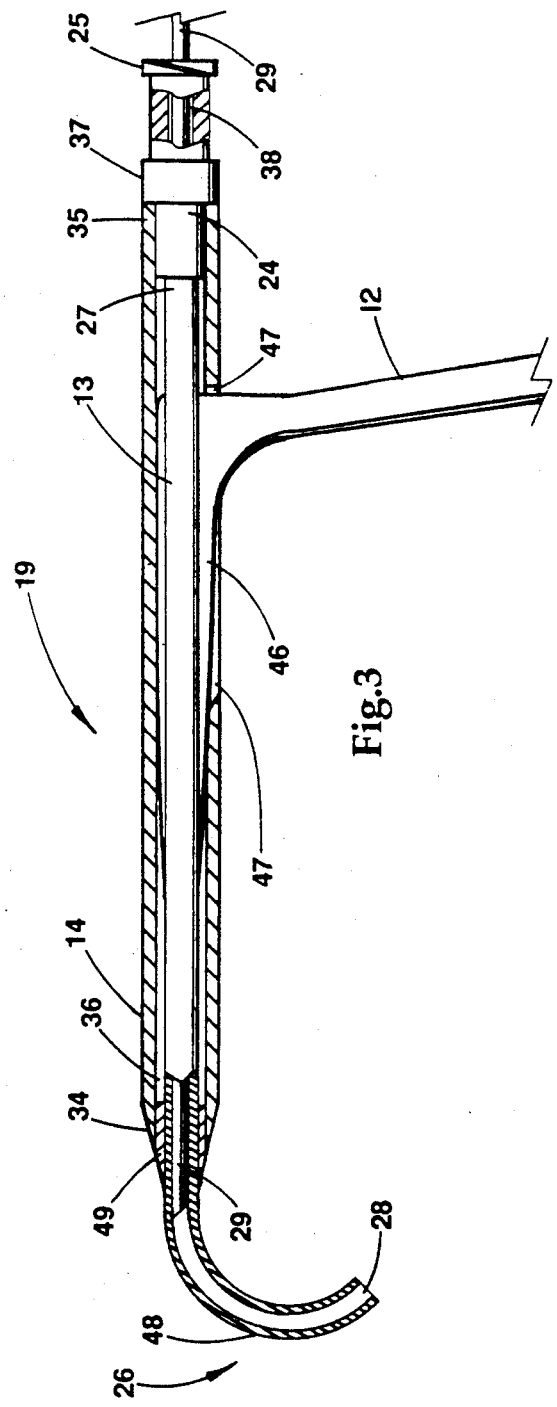
Fig. 2
Fig. 3

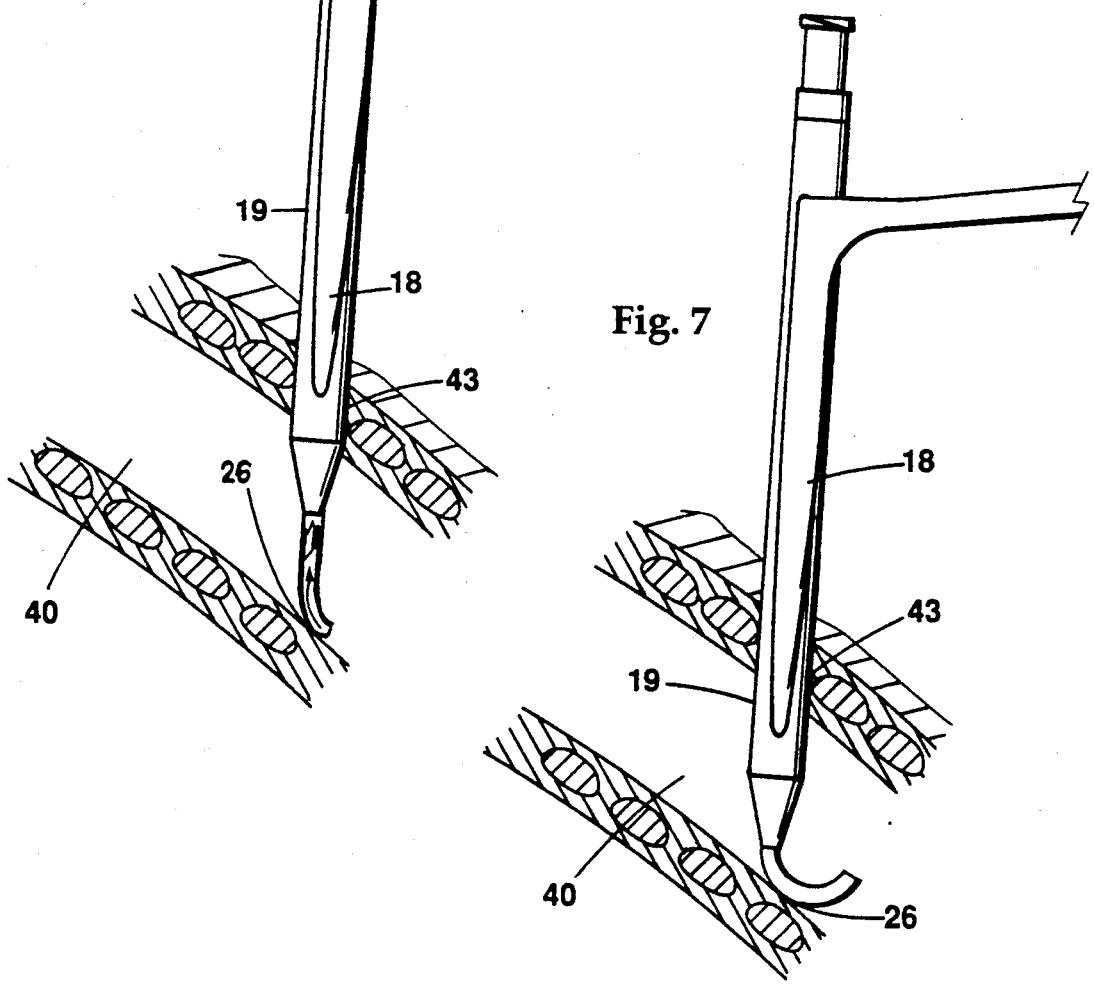

SPECULUM FOR FORMING AN OSTOMY IN A TRACHEA

TECHNICAL FIELD

This invention relates generally to medical devices for percutaneously accessing a patient's air passageway and atraumatically dilating the opening thereto, and, in particular, to a speculum for forming an ostomy in a trachea.

BACKGROUND OF THE INVENTION

An ostomy in a trachea bypasses an air passageway obstruction and maintains air flow to a patient. During tracheostomy and cricothyreotomy procedures, complications of injury and collapse of the trachea can result in permanent brain damage or death. These complications arise from trauma to surrounding tissue, an oversized opening of the trachea, or puncture of the posterior trachea wall. Furthermore, quick restoration of a patient's air passageway is critical.

Many approaches for forming an ostomy in a trachea require making an incision in the neck using a scalpel. In an elective tracheostomy, this surgical procedure is typically performed while the patient is under general anesthesia. Use of the scalpel potentially causes undue trauma to surrounding tissue and creates an oversized opening in the soft tissue of the neck. To minimize trauma, it is desirable that the incised opening be small and be enlarged with subsequent dilation.

One prior art technique of dilating an ostomy includes the use of a wire guide to facilitate the introduction of dilators into the trachea. As disclosed in U.S. Pat. No. 4,677,978, a needle and an over-the-needle catheter are inserted into the trachea. The needle is removed, and the catheter is replaced with a wire guide. A tapered, elongated, tubular dilator or a series of telescopically positionable, tapered dilators is positioned over the wire guide and introduced into the trachea. A problem with this technique is the sequential manipulation of several devices by the physician, which is time consuming and complicates the procedure. A modification to this technique eliminates the use of the catheter by placing a wire guide through the needle, as disclosed in U.S. Pat. No. 4,889,112. However, maintaining the point of entry to the trachea by holding the needle in the trachea while positioning a guide wire therethrough increases the risk of injuring the posterior trachea wall. If the needle advances too far, the posterior trachea wall will be perforated.

Another prior art technique of dilating an ostomy is the use of a tapered, elongated, tubular dilator or a series of telescopically positionable, tapered dilators with increasingly larger diameters. A problem with these dilators is that each dilator presents a pointed distal end to the posterior trachea wall when introduced into the trachea. The risk of injury to the trachea is compounded by the toughness of the trachea membrane, which resists the introduction of medical devices. Introducing these elongated dilators requires the application of considerable force. A physician must push the dilator into the trachea yet avoid puncturing the posterior trachea wall. Yet another prior art technique of dilating an ostomy includes the use of a device with a handle and nose, which extends laterally from the axis of the handle. The nose has two jaws that spread apart for separating tissue. This type of instrument offers more powerful dilation than is possible with elongated dilators. One device, for example, is introduced into the trachea by positioning the elongated, tapered nose over a wire guide, as in U.S. Pat. No. 4,889,112. A problem with this device is that the unguarded nose must be inserted with precision and manipulated at an angle to prevent perforating the posterior trachea wall. Another device, disclosed in U.S. Pat. No. 4,643,188, has a handle and laterally extending nose with two needle-like jaws. The jaws are tapered and terminate in sharpened, flat, distal blades. A problem with this device is that the jaws present sharpened, distal blades to the posterior trachea wall when introduced into the trachea. As a result, the blades can seriously injure or perforate the posterior trachea wall.

SUMMARY OF THE INVENTION

The foregoing problems are solved and a technical advance is achieved in an illustrative speculum for forming an ostomy in a trachea. The speculum comprises pivotally interconnected, opposing elongated members having respective proximal handle portions and distal nose portions extending distally from the elongated members. The nose portions are laterally angled with respect to the handle portions for controlled insertion of the nose portions into the trachea. The second nose portion includes a tubular member having a flexible distal end having a preformed curve and extending distally beyond the first nose portion for advantageously preventing trauma to the posterior trachea wall when the nose portions are pushed through the opening in the trachea. The speculum further comprises a cannula sized for extension through a passageway of the tubular member and straightening the preformed curve when extended entirely through the passageway. Connectors are attached about the proximal ends of the tubular member and the cannula and joined together for temporarily, fixedly positioning the cannula in the tubular member passageway.

The method of forming an ostomy in the trachea with the speculum includes introducing percutaneously a cannula and the distal end of the tubular member in a straightened configuration into the trachea until air bubbles form in a chamber of a syringe attached to the proximal end of the cannula. When bubbles form, the cannula is disengaged from the tubular member, and the distal nose portions of the speculum are introduced into the trachea through the opening. As the distal nose portions of the speculum are introduced into the trachea, the tubular member transitions from the straight configuration to the preformed curve for preventing trauma to the posterior wall of the trachea. With the distal nose portions of the speculum extended through the trachea opening, the distal nose portions are spread to laterally dilate the trachea opening. The speculum is rotated approximately 90 degrees, and the opening is dilated in the longitudinal direction with the distal nose portions. An ostomy tube is introduced into the trachea through the opening and between the separated distal nose portions. The method further comprises removing the speculum through the opening after the ostomy tube is positioned.

In one embodiment, a distal nose portion comprises a tubular sheath of which the tubular member is positioned therein. The tubular sheath is tapered at the distal end for insertion through the trachea opening. The tubular member is permanently fixedly positioned in a longitudinal recess of a distal nose portion extending distally from an elongated member.

The speculum also comprises a spring attached to at least one of the handle portions for urging the distal nose portions toward each other. A stop extending laterally between the proximal handle portions limits separation of the distal nose portions with respect to each other.

BRIEF DESCRIPTION OF THE DRAWING

FIG. 2 depicts a partial side view of the speculum of FIG. 1;

FIG. 3 depicts a partial, sectioned view of a nose portion of the speculum of FIGS. 1 and 2;

FIGS. 5-10 depict a method of forming an ostomy in a trachea using the speculum of FIG. 1.

DETAILED DESCRIPTION

Figure 1:
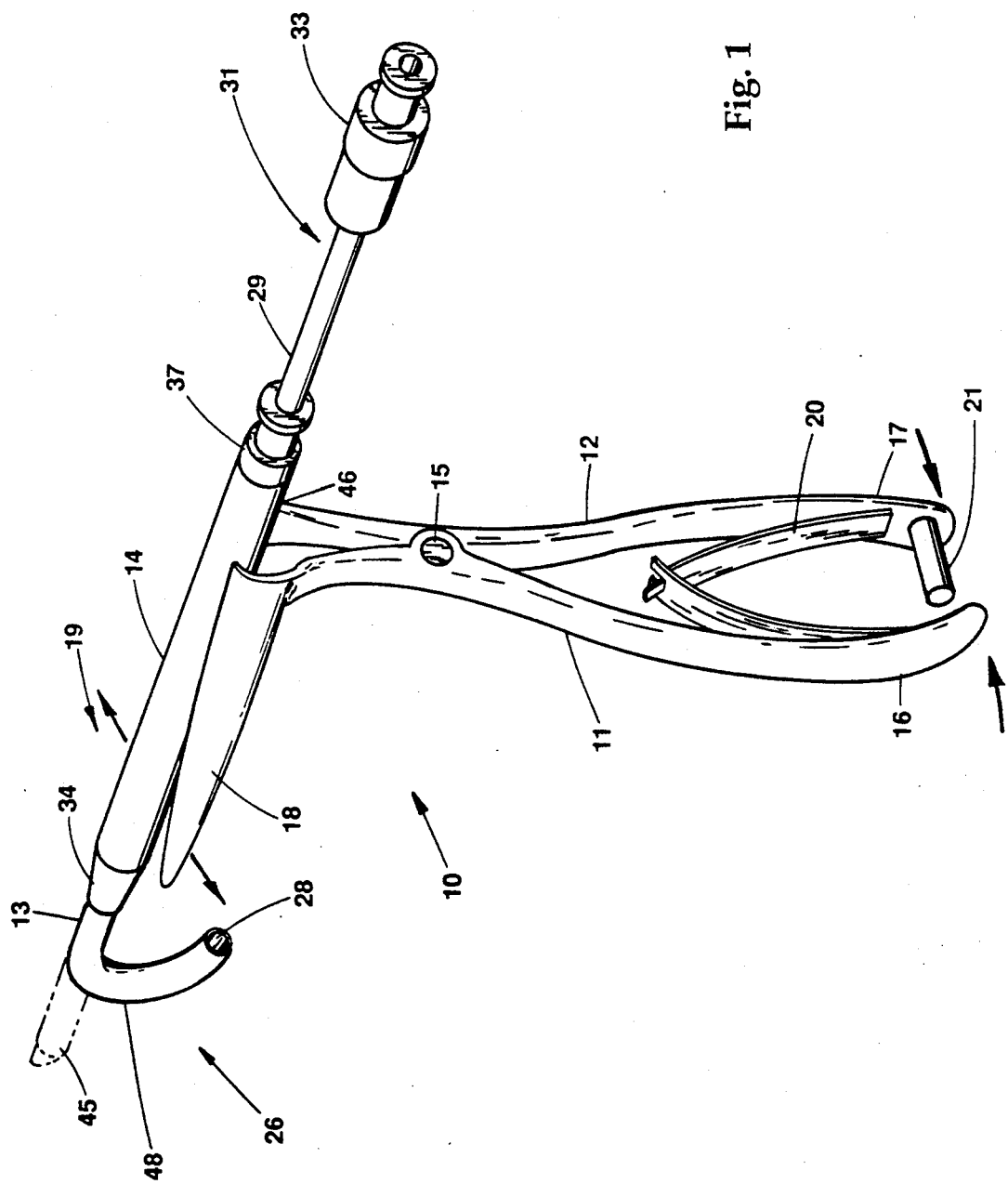
FIG. 1 depicts a speculum of the present invention.

Depicted in FIG. 1 is speculum 10 for forming an ostomy in a trachea. The speculum is used in tracheostomy and cricothyreotomy procedures and includes opposing elongated members 11 and 12 that are pivotally interconnected about the midpoint thereof by pivot pin 15. The speculum further includes proximal handle portions 16 and 17 for hand manipulation of the speculum by a physician. The speculum also comprises distal nose portions 18 and 19 extending distally from elongated members 11 and 12, respectively, for dilating a tracheal opening. The nose portions of the speculum are laterally angled with respect to the handle portions to enhance the physician's control during insertion and dilation. Extending distally from nose portion 19 and beyond nose portion 18 is tubular member 13 having flexible distal end 26 with a preformed curve which presents an atraumatic rounded surface 48 to the posterior trachea wall when the nose portions of the speculum are positioned in the trachea. The speculum further includes cannula 29 that is positionable through passageway 28 of the tubular member and extends distally therefrom for forming an opening in the trachea percutaneously through a patient's neck. When the cannula extends through the tubular member, the tubular member assumes a straight configuration for passage through the trachea opening, as shown by phantom lines 45. When the cannula and tubular member are percutaneously introduced into the air passageway of the trachea as evidenced by bubbles forming in the chamber of a syringe attached to the cannula, cannula connector hub 33 and tubular connector hub 37 are disengaged, and the cannula is partially or entirely removed from the tubular member so that the distal end of the tubular member assumes its preformed curve for preventing injury to the posterior trachea wall. The nose portions of the speculum are pushed into the tracheal opening and spread apart for dilating the opening in both the longitudinal and lateral directions. An ostomy tube is then positioned in the trachea through the opening between the separated nose portions, after which the speculum is removed.

Proximal handle portions 16 and 17 of interconnected members 11 and 12 form speculum handles for manipulation by a physician. Similarly, distal nose portion 18 is formed from the tapered distal nose portion of elongated member 11. Distal nose portion 19 of the speculum includes tubular sheath 14 with tapered distal nose portion 46 of elongated member 12 positioned in passageway 36 of the tubular sheath, as is more clearly shown in the partially sectioned view of distal nose portion 19 of the speculum in FIG. 3. Distal nose portion 46 of elongated member 12 extends laterally from passageway 36 and the tubular sheath via longitudinally extending slit 47. Distal end 34 of the tubular sheath is tapered for atraumatic dilation of the trachea opening.

A commercially available nasal speculum from, for example, Aesculap Instruments Corporation, Burlingame, Calif., comprises elongated members 11 and 12 of speculum 10. The elongated members include spring 20, which extends between the proximal handle portions for urging the distal nose portions of the speculum toward each other for insertion into and dilation of the trachea opening. The elongated members also include stop 21, which extends laterally between the proximal handle portions for limiting separation of the distal nose portions of the speculum with respect to each other, thereby preventing overdilation of the trachea opening. The distal nose portions of the speculum are illustrated as separated from each other in FIG. 1. However, distal nose portions 18 and 19 of the speculum are closed and in contact with each other when pushing cannula 29 having proximal end 31, tubular member 13, and distal nose portions 18 and 19 percutaneously through the opening into the trachea air passageway. When positioned in the opening, the distal nose portions of the speculum are separated by the physician squeezing the speculum handles to dilate the tracheal opening.

Depicted in FIG. 2 is a partial side view of speculum 10 with opposing distal nose portions 18 and 19 in contact with each other. Cannula 29 extends distally from the passageway of tubular member 13 and in a temporarily fixed position via joined together cannula connector hub 33 and tubular connector hub 37. By way of example, cannula 29 is a commercially available 12 cm, 14 gauge needle with a lancet bevel at distal end 30 for extending from and straightening the preformed curve of distal end 26 of tubular member 13. When straightened, tubular member 13 extends for approximately 3; mm from beveled distal end 34 of tubular sheath 14.

Depicted in FIG. 3 is a partially sectioned side view of distal nose portion 19. Cannula 29 is positioned partially therethrough. Tubular member 13 is permanently, fixedly positioned in a longitudinal recess of distal nose portion 46 of elongated member 12 by tubular sheath 14 and commercially available medical grade adhesive 49, such as Loctite adhesive #401, positioned in passageway 36 about tapered distal end 34 of tubular sheath 14. Tubular member 13 is an 8 French diameter FEP TEFLON ® material tube approximately 4" in length with a wall thickness of 0.012". Tubular member 13 includes flexible distal end 26 having curved, rounded surface 48, proximal end 27, and passageway 28 extending therethrough. Preformed distal end 26 has a maximum arc length of 2 cm. Tubular sheath 14 is a 15 French diameter FEP TEFLON material tube approximately 3" in length with a wall thickness of 0.012". Longitudinally extending slit 47 in tubular sheath 14 is long enough to insert distal nose portion 46 of elongated member 12 into passageway 36 of the sheath. Tubular sheath 14 includes tapered distal end 34, proximal end 35, and passageway 36 extending therethrough. Tapered distal end 34 of the sheath tapers from a 15 French to a 8 French outside diameter. Connector hub 37 is fixedly attached about the proximal ends of tubular sheath 14 and tubular member 13. Connector hub 37 includes a longitudinally extending passageway 38 which communicates with passageway 28 of tubular member 13. Connector hub 37 further includes a well-known distal end cap 24 for securing the proximal end of tubular member 13 therein. Distal end cap 24 is inserted into the proximal end of tubular sheath 14. The proximal end of the tubular sheath is affixed to the end cap using, for example, a commercially available medical grade adhesive. Connector hub 37 includes a flared flange fitting 25, such as a well-known Luer lock fitting, for forming a locking mechanism that joins together with the cannula connector hub for temporarily, fixedly positioning the cannula in the tubular member passageway.

Figure 4:
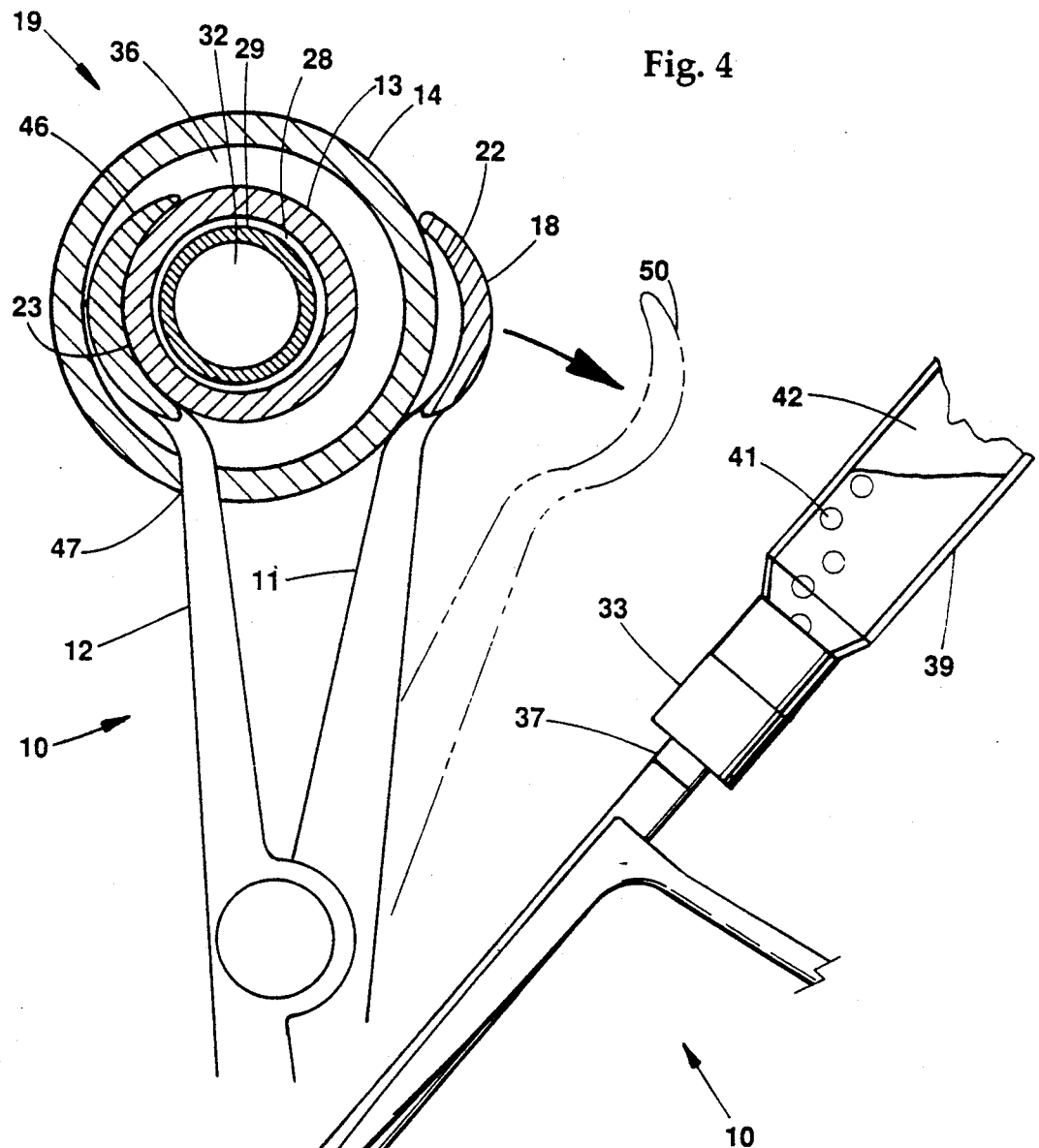
FIG. 4 depicts a partial, cross-sectional view of the speculum of FIG. 1 taken along the lines 4—4.

Depicted in FIG. 4 is a partial, cross-sectional view of speculum 10 of FIG. 2 taken along the lines 4—4 to further illustrate the placement of tubular member 13, tubular sheath 14, and cannula 29 with respect to distal nose portions 18 and 19 of the speculum. Distal nose portion 19 of the speculum includes distal nose portion 46 of elongated member 12. Distal nose portions 18 and 46 of respective elongated members 11 and 12 include respective opposing faces 22 and 23 with longitudinal recesses formed therein. Tubular member 13 is positioned in longitudinally recessed face 23 and permanently, fixedly held in place via tubular sheath 14 as previously described. Cannula 29 includes passageway 32 and extends through passageway 28 of the tubular member. Distal nose portion 46 extends longitudinally through passageway 36 of the tubular sheath and extends laterally therefrom via slit 47. In the closed position, laterally opposing nose portion 18 contacts the outer surface of tubular sheath 14 for percutaneous insertion through the tracheal opening. To dilate the opening, the handles are squeezed by the physician to separate distal nose portion 18 from tubular sheath 14, as shown by phantom lines 50.

Figure 5:
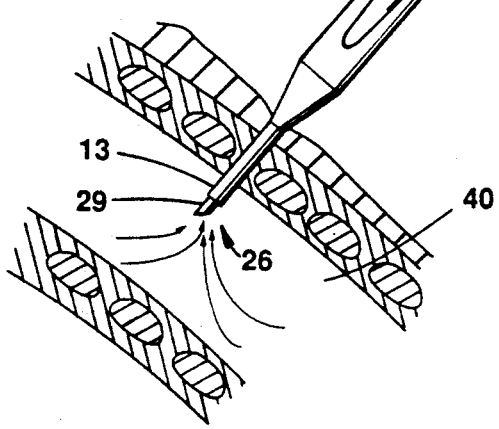

Depicted in FIGS. 5–10 is a method of forming an ostomy in a trachea. FIG. 5 depicts speculum 10 with cannula 29 fixedly positioned therein, preformed distal end 26 of tubular member 13 in a straightened configuration, and syringe 39 securably attached to connector hub 33 of the cannula via a distal syringe connector. When attached, cannula 29 and tubular member 13 are percutaneously introduced at a right angle into trachea air passageway 40. When air bubbles 41 appear in chamber 42 of the syringe, connector hub 33 of the cannula is detached from connector hub 37 of the speculum, thereby disengaging the cannula from the tubular member.

As depicted in FIGS. 6 and 7, laterally opposing distal nose portions 18 and 19 are introduced at an acute angle into trachea air passageway 40 via trachea opening 43. During this phase of the procedure, preformed distal end 26 begins transitioning from a straightened to the preformed curve configuration. When connector hub 33 of the cannula is detached from connector hub 37 of the speculum, the cannula can extend partially through the tubular member without posing the risk of puncturing the posterior trachea wall. The cannula can also be removed if time permits.

Figure 8:
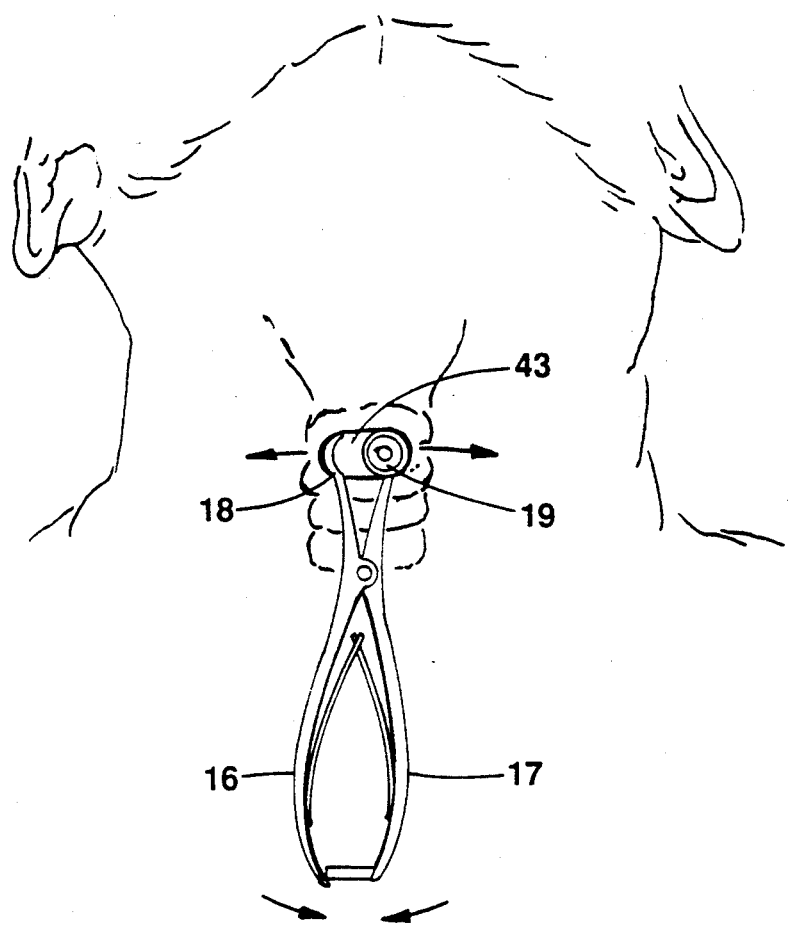

FIG. 8 depicts distal nose portions 18 and 19 spread apart from each other for laterally dilating opening 43 to the trachea. Distal nose portions are separated by squeezing opposing proximal handle portions 16 and 17.

Figure 9:
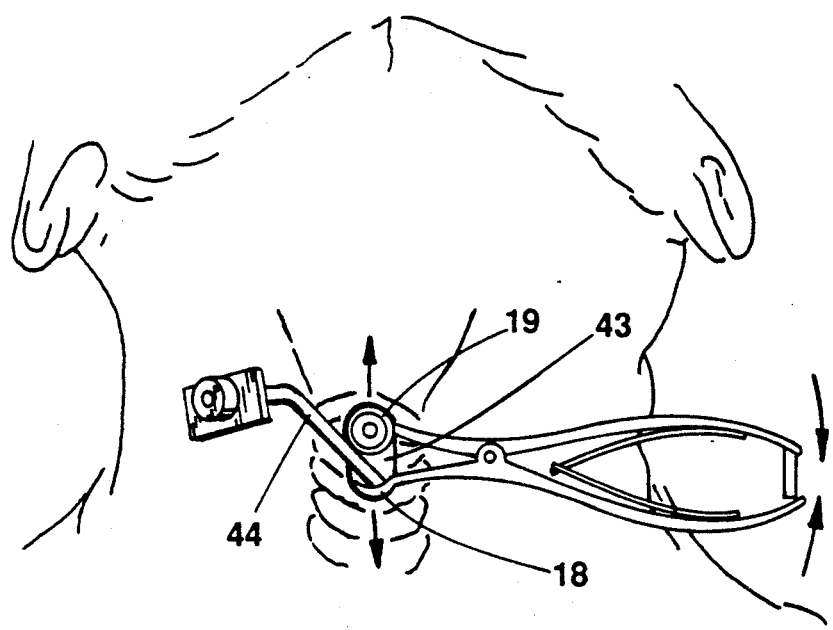

FIG. 9 depicts distal nose portions 18 and 19 spread apart from each other for longitudinally dilating opening 43 to the trachea. Ostomy tube 44 is introduced into the trachea through opening 43 and spread-apart nose portions 18 and 19.

Figure 10:
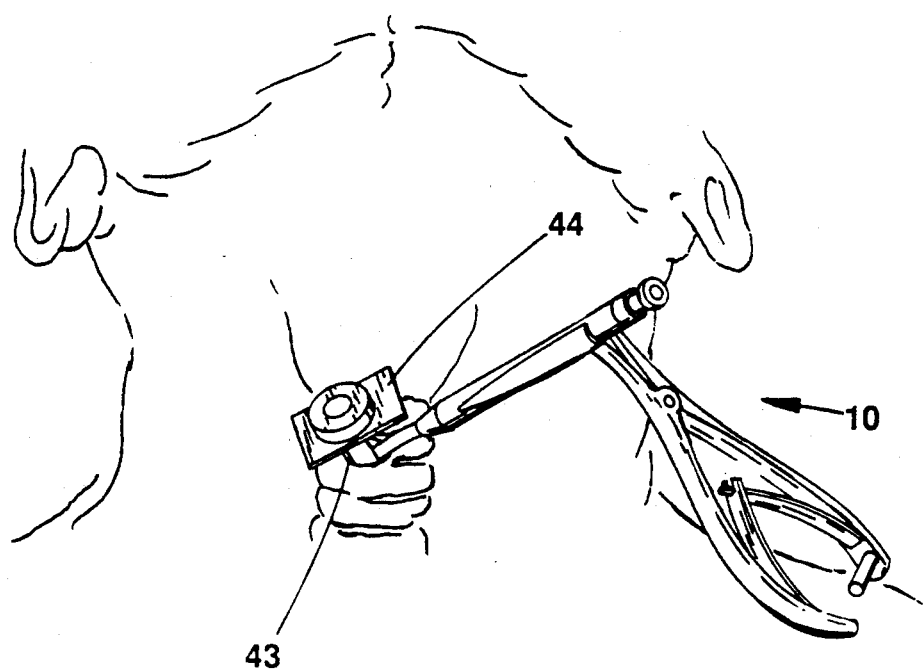

FIG. 10 depicts ostomy tube 44 fully positioned in opening 43. Speculum 10 is then removed from the trachea and opening 43.

While the speculum and method of use have been illustrated and described in detail in the drawing and foregoing description, the same is to be considered illustrative and not restrictive in character, it being understood that only the preferred embodiment has been shown and that all changes and modifications that come within the spirit of the invention are desired to be protected. In particular, it is further contemplated that the tubular member is integrally formed with one of the distal nose portions, and the tubular sheath is eliminated. Alternatively, the tubular sheath is integrally formed as one of the distal nose portions and the tubular member is positioned and permanently, fixedly attached therein. It is also contemplated that the dimensions of the nose portions, tubular member, and tubular sheath may be modified for performing an emergency cricothyreotomy or for forming an ostomy in the trachea of a pediatric patient.

What is claimed is:

1. A speculum for forming an ostomy in a trachea comprising:
    first and second opposing elongated members pivotally interconnected and having respective first and second proximal handle portions;
    first and second distal nose portions extending distally from said first and second members, respectively, and laterally angled with respect to said handle portions; and
    said second nose portions including a tubular member having a first proximal end, a flexible distal end having a preformed curve and extending distally beyond said first nose portion for insertion through said ostomy, and a passageway extending longitudinally between said distal and proximal ends; said tubular member being permanently, fixedly positioned to said second nose portion.

2. The speculum of claim 1 further comprising a cannula sized for extension through said passageway of said tubular member, said cannula straightening said preformed curve of said tubular member when extended through said passageway.

3. The speculum of claim 2 wherein said cannula includes a distal end, a proximal end, a longitudinal passageway extending therethrough, and a first connector permanently, fixedly positioned about said proximal end for temporarily, fixedly positioning said cannula in said passageway of said tubular member when said cannula is positioned in said passageway of said tubular member.

4. The speculum of claim 3 further comprising a syringe connectable to said first connector and having a chamber communicating with said passageway of said cannula when said syringe is connected to said first connector.

5. The speculum of claim 4 further comprising a tubular sheath positioned around said second nose portion and having a tapered distal end, a proximal end, and a passageway extending longitudinally therebetween.

6. The speculum of claim 5 further comprising a second connector positioned about said proximal ends of said tubular member and said tubular sheath and having a connector passageway extending therethrough and communicating with said passageway of said tubular member, at least one of said first and second connectors having a locking mechanism for temporarily, fixedly positioning said cannula in said passageway of said tubular member when said first and second connectors are joined together.

7. The speculum of claim 4 further comprising a second connector positioned about said proximal end of said tubular member and having a connector passageway extending therethrough and communicating with said passageway of said tubular member, at least one of said first and second connectors having a locking mechanism for temporarily, fixedly positioning said cannula in said passageway of said tubular member when said first and second connectors are joined together.

8. The speculum of claim 1 further comprising a spring attached to at least one of said first and second handle portions for urging said distal nose portions toward each other.

9. The speculum of claim 1 further comprising a stop extending laterally between said proximal handle portions and limiting separation of said first and second distal nose portions with respect to each other.

10. A speculum for forming an ostomy in a trachea comprising:
   first and second opposing elongated members pivotally interconnected and having respective first and second proximal handle portions and respective first and second tapered distal nose portions, said nose portions being laterally angled with respect to said handle portions, said first and second nose portions having respective first and second opposing faces and respective first and second recesses extending longitudinally therein;
   a tubular member permanently, fixedly positioned within said second longitudinal recess and having a proximal end, a flexible distal end having a preformed curve extending distally beyond said first nose portion for insertion through said ostomy, and a passageway extending longitudinally therethrough; and
   a tubular sheath positioned around said second nose portion and said tubular member and having a tapered distal end, a proximal end, and a passageway extending longitudinally therethrough.

11. The speculum of claim 10 further comprising a cannula sized for extension through said passageway of said tubular member, said cannula straightening said preformed curve of said tubular member when extended through said passageway of said tubular member.

12. The speculum of claim 11 wherein said cannula includes a distal end, a proximal end, a proximal end, a longitudinal passageway extending therethrough, and a first connector permanently, fixedly positioned about said proximal end of said cannula for temporarily, fixedly positioning said cannula in said passageway of said tubular member when said cannula is positioned in said passageway of said tubular member.

13. The speculum of claim 12 further comprising a syringe connectable to said first connector and having a chamber communicating with said passageway of said cannula when said syringe is connected to said first connector.

14. The speculum of claim 13 further comprising a second connector positioned about said proximal ends of said tubular member and said tubular sheath and having a passageway extending therethrough and communicating with said passageway of said tubular member, at least one of said first and second connectors having a locking mechanism for temporarily, fixedly positioning said cannula in said passageway when said first and second connectors are joined together.

15. The speculum of claim 14 further comprising a spring attached to at least one of said first and second handle portions for urging said distal nose portions toward each other.

16. A speculum for forming an ostomy in a trachea comprising:
   first and second opposing elongated members pivotally interconnected and having respective first and second proximal handle portions;
   first and second distal nose portions extending distally from said first and second members, respectively, and laterally angled with respect to said handle portions; and
   said second nose portions including a tubular sheath including a tubular member permanently, fixedly positioned therein and having a proximal end, a flexible distal end having a preformed curve and extending distally beyond said first nose portion for insertion through said ostomy, and passageway extending longitudinally between said distal and proximal ends.

17. A speculum for forming an ostomy in a trachea comprising:
   first and second opposing elongated members pivotally interconnected and having respective first and second proximal handle portions and respective first and second tapered distal nose portions laterally angled with respect to said handle portions, said first and second nose portions having respective first and second opposing faces and respective first and second recesses extending longitudinally therein;
   a tubular member permanently, fixedly positioned within said second longitudinal recess and having a proximal end, a flexible distal end having a preformed curve extending distally beyond said first nose portion for insertion through said ostomy, and a passageway extending longitudinally therethrough;
   a tubular sheath positioned around said second nose portion and said tubular member and having a tapered distal end, a proximal end, and a passageway extending longitudinally therethrough.
   a first connector positioned about said proximal ends of said tubular member and said tubular sheath and having a connector passageway extending therethrough and communicating with said passageway of said tubular member;
   a cannula sized for extension through said passageway of said tubular member and including a distal end, a proximal end, a longitudinal passageway extending therethrough, and a second connector permanently, fixedly positioned about said proximal end of said cannula for temporarily, fixedly positioning said cannula in said passageway of said tubular member, said cannula straightening said preformed curve of said tubular member when extended through said passageway of said tubular member, at least one of said first and second connectors having a locking mechanism for temporarily, fixedly positioning said cannula in said passageway of said tubular member when said first and second connectors are joined together;

a syringe having a distal end connector and a chamber therein communicating with said passageway of said cannula through said distal end connector when said distal end connector and said second connector are joined together;

a spring attached to at least one of said first and second handle portions for bringing said distal nose portions toward each other; and a stop extending laterally between said proximal handle portions and limiting separation of said first and second distal nose portions with respect to each other.

18. Method of forming an ostomy in a trachea comprising the steps of:

providing a speculum having first and second elongated members pivotally interconnected;

providing respective first and second proximal handle portions;

providing first and second distal nose portions extending distally from said first and second members, respectively, and laterally angled with respect to said handle portions;

providing a fixedly positioned tubular member on said second nose portion;

providing said tubular member with a proximal end, a flexible distal end having a preformed curve, and a longitudinal passageway extending therebetween;

providing a cannula positionable within said passageway of said tubular member;

providing a syringe having a chamber communicating with said passageway of said cannula, straightening said preformed curve of said tubular member by inserting said cannula through said tubular member;

attaching said cannula to said tubular member;

introducing percutaneously said cannula and said distal end of said tubular member in a straight configuration into said trachea until air bubbles form in said chamber of said syringe;

disengaging said cannula from said tubular member;

introducing said distal nose portions of said speculum into said trachea, whereby said distal end of said tubular member transitions from said straight configuration to said preformed curve during introduction of said distal nose portions of said speculum into said trachea;

laterally dilating said opening in said trachea with said distal nose portions;

longitudinally dilating said opening in said trachea with said distal nose portions; and introducing into said trachea an ostomy tube through said opening and between said distal nose portions.

19. The method of claim 18 further comprising removing said speculum from said opening after said ostomy tube is positioned in said trachea through said opening.

20. The method of claim 18 further comprising the step of removing said cannula from said passageway of said tubular member after said distal end of said tubular member has transitioned from said straight configuration to said preformed curve.

* * * * *